United States Patent [19]

Alig et al.

[11] Patent Number: 5,071,860
[45] Date of Patent: Dec. 10, 1991

[54] INSECTICIDALLY ACTIVE SUBSTITUTED HETEROARYL PHENYL ETHERS

[75] Inventors: Bernd Alig, Koenigswinter; Wilhelm Stendel, Wuppertal; Michael Londershausen, Erkrath, all of Fed. Rep. of Germany

[73] Assignee: Bayer Aktiengesellschaft, Leverkusen, Fed. Rep. of Germany

[21] Appl. No.: 490,027

[22] Filed: Mar. 7, 1990

[30] Foreign Application Priority Data

Mar. 15, 1989 [DE] Fed. Rep. of Germany ....... 3908452
Apr. 7, 1989 [DE] Fed. Rep. of Germany ....... 3911217
Oct. 24, 1989 [DE] Fed. Rep. of Germany ....... 3935287

[51] Int. Cl.$^5$ .................... A61K 31/445; C07D 401/12
[52] U.S. Cl. .................................... 514/332; 514/335;
514/345; 514/348; 514/350; 514/351; 514/354;
514/355; 514/357; 544/235; 544/237; 544/238;
544/239; 544/240; 544/241; 544/283; 544/284;
544/285; 544/286; 544/287; 544/295; 544/296;
544/298; 544/299; 544/300; 544/309; 544/310;
544/315; 544/318; 544/319; 544/353; 544/354;
544/355; 544/356; 544/357; 544/405; 544/406;
544/408; 544/409; 546/140; 546/141; 546/142;
546/145; 546/146; 546/148; 546/149; 546/153;
546/155; 546/156; 546/168; 546/176; 546/180;
546/261; 546/262; 546/264; 546/266; 546/296;
546/298; 546/300; 546/301; 546/302; 546/179;
546/186; 546/189; 546/200; 546/203; 546/219;
546/225; 546/226; 546/285; 548/156; 548/169;
548/173; 548/174

[58] Field of Search ............... 546/261, 262, 264, 266, 546/296, 298, 300, 301, 302; 514/332, 335, 345, 348, 350, 351, 354, 355, 357

[56] References Cited

FOREIGN PATENT DOCUMENTS 0128648 12/1984 European Pat. Off. .
0218543 4/1987 European Pat. Off. .
0255935 2/1988 European Pat. Off. .
2520145 11/1975 Fed. Rep. of Germany .
2520177 11/1975 Fed. Rep. of Germany .

OTHER PUBLICATIONS

Patent Abstracts of Japan, vol. 9, No. 96, Apr. 25, 1985 (C-278) (1819); & JP-A-59227861 (Mitsui Toatsu Kagaku K.K.) 12/21/84.

*Primary Examiner*—C. Warren Ivy
*Assistant Examiner*—James H. Turnipseed
*Attorney, Agent, or Firm*—Sprung Horn Kramer & Woods

[57] ABSTRACT

Insecticidally active substituted heteroaryl phenyl ethers of the formula

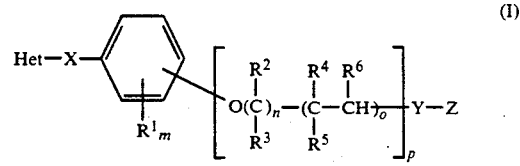

(I)

in which
Het represents an optionally substituted heteroaromatic radical,
X represents O, S, —CH$_2$—, —O—CH$_2$—, —S—CH$_2$—, —CH$_2$—O—,

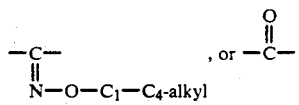

Y represents O, —O—CH$_2$— or S,
Z represents an optionally substituted aromatic or heteroaromatic radical;
m represents integers from 1–4
n represents 0, 1, 2, 3, 4
O represents 0, 1, 2, 3, 4, provided than n and o do not simultaneously represent 0
p represents integers from 1–4,
R$^2$, R$^3$, R$^4$, R$^5$ and R$^6$ independently of one another represent hydrogen, C$_1$–C$_6$-alkyl which is optionally substituted; two radicals adjacent to one another can also, together with the C atoms to which they are bonded, form a saturated carbocyclic 5- or 6-ring,
R$^1$ represents identical or different radicals hydrogen, halogen, CN, C$_{1-4}$-alkyl, 1-5-halogeno-C$_{1-4}$-alkyl, C$_{1-4}$-alkoxy, C$_{1-4}$-alkylthio, 1-5-halogeno-C$_{1-4}$-alkoxy, 1-5-halogeno-C$_{1-4}$-alkylthio, phenyl or phenoxy radicals.

The compounds can optionally be present in the form of their enantiomers, racemates or diastereomers.

8 Claims, No Drawings

INSECTICIDALLY ACTIVE SUBSTITUTED HETEROARYL PHENYL ETHERS

The present invention relates to substituted heteroaryl phenyl ethers, processes for their preparation and their use as insecticides.

Substituted diphenyl ethers and their use as insecticides have already been disclosed. However, their action, above all against the different stages of development of fleas, is not satisfactory in every case (DE-PS 2,520,145, EP-OS 128,648).

The present invention relates to 1. New substituted heteroaryl phenyl ethers of the formula (I)

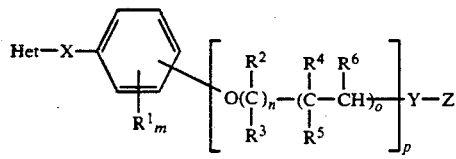

(I)

in which

Het represents an optionally substituted heteroaromatic radical,

X represents O, S, —CH$_2$—, —O—CH$_2$—, —S—CH$_2$—, —CH$_2$—O—,

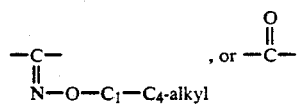

Y represents O, —O—CH$_2$— or S,

Z represents an optionally substituted aromatic or heteroaromatic radical;

m represents integers from 1–4 n represents 0, 1, 2, 3, 4 o represents 0, 1, 2, 3, 4, provided that n and o do not simultaneously represent 0 p represents integers from 1–4

R$^2$, R$^3$, R$^4$, R$^5$ and R$^6$ independently of one another represent hydrogen, C$_1$-C$_6$-alkyl which is optionally substituted by halogen or C$_{1-4}$-alkoxy; two radicals adjacent to one another can also, together with the C atoms to which they are bonded, form a saturated carbocyclic 5- or 6-ring, R$^1$ represents identical or different radicals from the group comprising hydrogen, halogen, CN, C$_{1-4}$-alkyl, 1-5-halogeno-C$_{1-4}$-alkyl, C$_{1-4}$-alkoxy, C$_{1-4}$-alkylthio, 1-5-halogeno-C$_{1-4}$-alkoxy, 1-5-halogeno-C$_{1-4}$-alkylthio, phenyl or phenoxy, where the compounds of the formula I can optionally be present in the form of their enantiomers, racemates or diastereomers.

2. Process for the preparation of the substituted heteroaryl phenyl ethers of the formula (I)

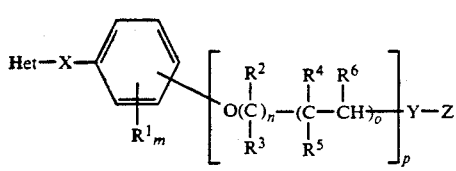

(I)

characterized in that a) heteroaryl phenol ethers of the formula (II)

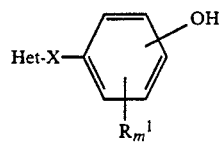

(II)

in which

Het, X, R$^1$ and m have the abovementioned meaning, are reacted with compounds of the formula (III)

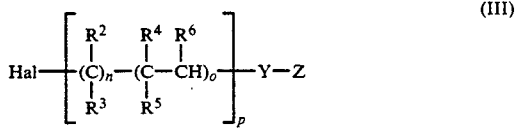

(III)

in which

Hal represents halogen and Y, Z, R$^2$–R$^6$, n, o and p have the abovementioned meaning, or b) compounds of the formula (IV)

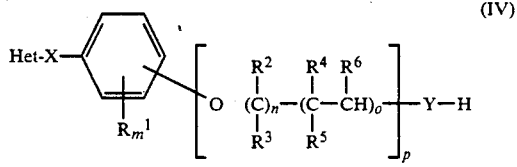

(IV)

in which

X, Het, R$^1$–R$^6$, m, n, o or p have the abovementioned meaning and

Y represents O or S are reacted with compounds of the formula (V)

Hal—Z or Hal—CH$_2$—Z    (V)

in which

Hal represents halogen,

Z has the abovementioned meaning, or c) compounds of the formula (VI)

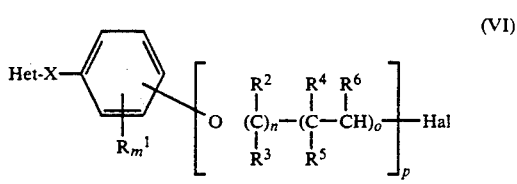

(VI)

in which

Hal represents halogen,

X, Het, R$^1$–R$^6$, m, n, o, and p have the abovementioned meaning, are reacted with compounds of the formula (VII)

H—Y—Z    (VII)

in which

Y and Z have the abovementioned meaning, or d) in the case in which Het and Z represent identical heterocycles, compounds of the formula (VIII)

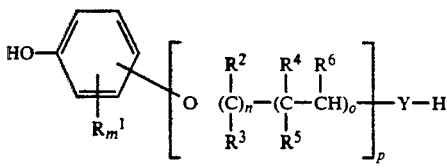

in which $R^1$-$R^6$, m, n, o and p have the abovementioned meaning and

Y represents O or S, are reacted with heterocyclic compounds of the formula (IX)

$$\text{Het—Hal or Het—CH}_2\text{—Hal} \tag{IX}$$

in which

Hal represents halogen, and

Het has the abovementioned meaning.

The compounds of the formula I and their salts with acids are suitable for combating insects. They can be employed particularly preferably for combating fleas, in particular against *Pulex irritans, Xenopsylla cheopis, Ctenocephalides canis, Ctenocephalides felis, Ceratophyllus gallinae, Echidnophaga gallinacea* or *Tunga penetrans*. The compounds of the formula I have properties inhibiting the development of insects. They can therefore be employed against all or individual stages of development of insects, in particular of the flea.

Heteroaromatic radicals within the meaning of Het or Z which may preferably be mentioned are the nitrogen heterocycles such as pyridyl, pyrimidinyl, pyrazinyl, pyridazinyl, quinolyl, isoquinolyl, phthalazinyl, naphthyridyl, quinoxalinyl, quinazolinyl, cinnolinyl, thiazolyl, benzothiazolyl, oxazolyl, benzoxazolyl, pyrazolyl, imidazolyl, benzimidazolyl as well as heterocycles such as furyl, thienyl, benzofuranyl or benzothienyl which are bonded to the other radical of the compound of the formula (I) via a C atom of the heterocycles.

The heteroaromatic radicals within the meaning of Het or Z can independently of one another be monosubstituted or polysubstituted by halogen, in particular chlorine, bromine, fluorine, $C_{1-4}$-alkyl, 1-5-halogeno-$C_{1-4}$-alkyl, $C_{1-4}$-alkoxy, 1-5-halogeno-$C_{1-4}$-alkoxy, $C_{1-4}$-alkylthio, 1-5-halogeno-$C_{1-4}$-alkylthio, nitro, CN, $C_{1-4}$-alkoxycarbonyl, amino, acylamino.

An aromatic radical within the meaning of Z which may preferably be mentioned is pheny, which may optionally be substituted by one or more of the substituents indicated under Het (above).

Preferred compounds are those of the formula (I) in which: Het represents optionally substituted nitrogen-containing heteroaromatics which are bonded via a C atom of the hetero ring to the other radical of the molecule. Those which may be mentioned in particular are: pyridyl, pyrimidinyl, pyrazinyl, pyridazinyl and thiazolyl, which can optionally be fused to a phenyl ring;

Substituents which may be mentioned are halogen, in particular fluorine, chlorine, bromine, $C_{1-4}$-alkyl, in particular methyl, 1-5-halogeno-$C_{1-2}$-alkyl, in particular trifluoromethyl, $C_{1-4}$-alkoxy, in particular methoxy, ethoxy, $C_{1-4}$-alkylmercapto, in particular methylmercapto, 1-3-halogeno-$C_{1-2}$-alkoxy, in particular trifluoromethoxy and 1-3-halogeno-$C_{1-2}$-alkylmercapto.

X represents 0;

$R^1$ represents identical or different radicals from the group comprising hydrogen, halogen, in particular chlorine or fluorine, CN, $C_{1-4}$-alkyl, in particular methyl, ethyl, t-butyl, $C_{1-4}$-alkoxy, in particular methoxy, 1-3-halogeno-$C_{1-2}$-alkoxy, in particular trifluoromethoxy, or phenyl;

m represents integers from 1–4 n represents 0, 1, 2, 3, 4

0 represents 0, 1, 2, 3, 4, provided that n and o do not simultaneously represent 0 p represents integers from 1–4;

$R^2$, $R^3$, $R^4$, $R^5$ and $R^6$ independently of one another represent hydrogen, $C_{1-4}$-alkyl, in particular methyl, 1-3-halogeno-$C_{1-2}$-alkyl, in particular trifluoromethyl, $C_{1-2}$-alkoxy-$C_{1-4}$-alkyl, in particular methoxymethyl, ethoxymethyl, i-propoxymethyl or t-butoxymethyl;

m represents integers from 1–4 n represents 0, 1, 2, 3, 4

0 represents 0, 1, 2, 3, 4, provided that n and o do not simultaneously represent O p represents integers from 1–4.

In particular, the following part of the formula

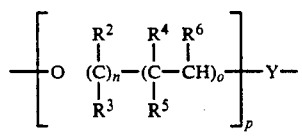

represents one of the following structures:

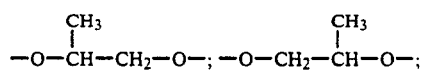

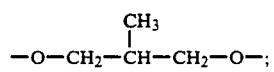

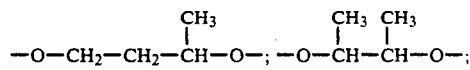

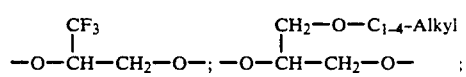

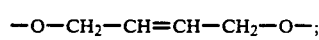

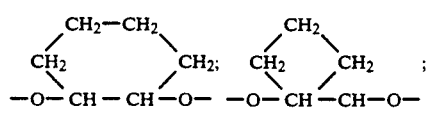

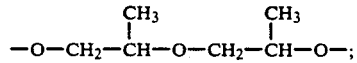

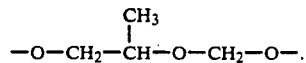

Z preferably represents one of the heteroaromatics indicated in the preferred definition of Het, which can optionally be substituted by one or more of the substituents indicated there. In addition, Z preferably represents phenyl which is optionally substituted by one or more of the substituents indicated under Het and also optionally by methylenedioxy, ethylenedioxy or dihalogenomethylenedioxy.

Particularly preferred compounds are those of the formula (I), in which

Het represents optionally substituted pyridyl, pyrimidinyl, pyrazinyl, thiazolyl or benzothiazolyl, which are bonded to the other radical of the compound of the formula (I) via a C atom of the heteroaromatic. Substituents which may be mentioned in particular are: chlorine, bromine, methyl, ethyl, trifluoromethyl and methoxy.

X represents O;

R¹ represents hydrogen;

the following part of the formula (I)

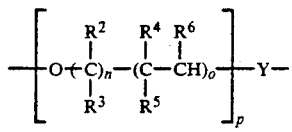

is in the para- or meta-position to the radical Het-X- and represents one of the following structures:

$$-O-CH_2-CH_2-O-; \quad -O-\underset{\underset{CH_3}{|}}{CH}-CH_2-O;$$

$$-O-CH_2-\underset{\underset{CH_3}{|}}{CH}-O-; \quad -O-CH_2-\underset{\underset{CF_3}{|}}{CH}-O-;$$

$$-O-CH_2-CH_2-O-CH_2-; \quad -O-(CH_2)_3-O-;$$

Z in particular represents optionally substituted pyridyl, pyrimidinyl or pyrazinyl, which are bonded to the other radical of the compound of the formula (I) via a C atom and also optionally substituted phenyl. Substituents which may be mentioned are: fluorine, chlorine, bromine, methyl or trifluoromethyl.

Those compounds which may be mentioned in particular are:

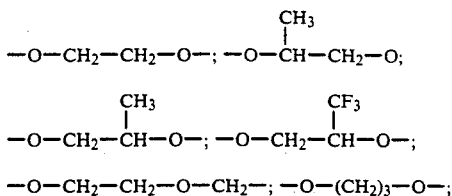

| X | R¹ | B | Het |
|---|---|---|---|
| O | 1,3-Cl₂ | —CH₂—CH—<br>        \|<br>        C₂H₅ | 2-pyridyl |
| S | H | —CH₂—CH—<br>        \|<br>        CF₃ | pyrazinyl |
| O | 1,3-Cl₂ | —CH₂—CH—<br>        \|<br>        CH₂F | 2-pyridyl |
| O | 1,3-Cl₂ | —CH₂—CH—<br>        \|<br>        CH₂—F | 3-pyridyl |
| S | 1,3-Cl₂ | —CH₂—CH—<br>        \|<br>        CH₂—F | 2-pyridyl |
| O | 3-Br | —CH₂—CH—<br>        \|<br>        CH₂—F | 2-pyridyl |
| CH₂ | 1,3-Cl₂ | —CH₂—CH—<br>        \|<br>        CH₂—F | 2-pyridyl |
| CH₂ | H | —CH₂—CH—<br>        \|<br>        CH₂—F | 2-pyridyl |

-continued
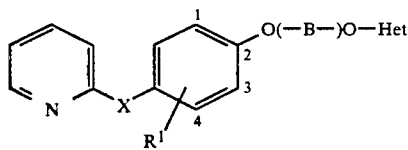
| X | R¹ | B | Het |
|---|---|---|---|
| O | H | $-CH_2-CH(CH_2F)-$ | 2-pyridyl |
| S | H | $-CH_2-CH(CH_2F)-$ | 2-pyridyl |
| O | 1,3-Cl₂ | $-CH_2-CH(CH_2F)-$ | 4-pyridyl |
| O | 1,3-Cl₂ | $-CH_2-CH(CH_3)-$ | 6-methyl-3-(2,6-dimethylmorpholin-4-yl)pyridazine |
| S | 1,3-Cl₂ | $-CH_2-CH(CH_3)-$ | 6-methyl-3-(2,6-dimethylmorpholin-4-yl)pyridazine |
| CH₂ | 1,3-Cl₂ | $-CH_2-CH(CH_3)-$ | 6-methyl-3-(2,6-dimethylmorpholin-4-yl)pyridazine |
| O | H | $-CH_2-CH(CH_3)-$ | 6-methyl-3-(2,6-dimethylmorpholin-4-yl)pyridazine |
| O | 1,3-Cl₂ | $-CH_2CH_2OCH(CH_3)CH_2-CH_2-$ | 2-pyridyl |

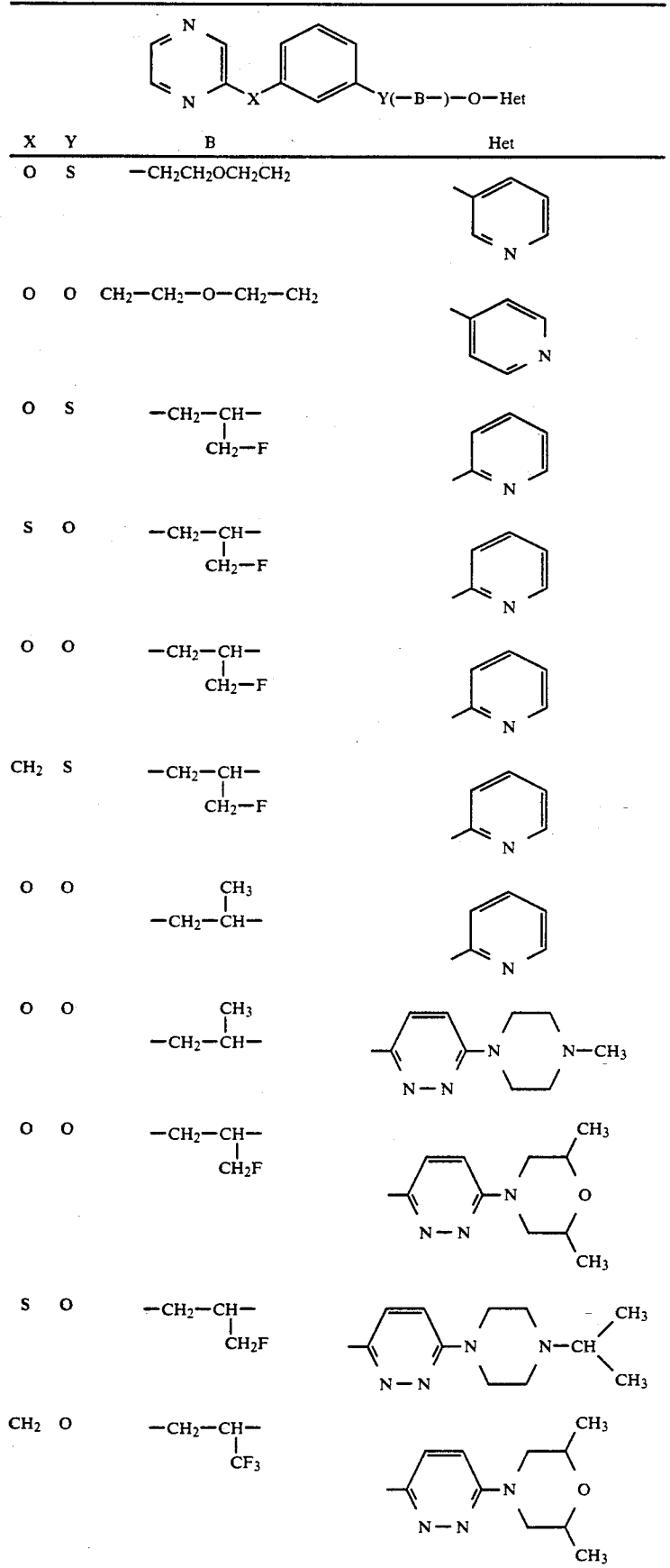

-continued

| X | Y | B | Het |
|---|---|---|---|
| O | O | —CH₂—CH(CF₃)— | morpholinyl-pyridazinyl |
| O | O | —CH₂—CH(CCl₃)— | bis(methyl)morpholinyl-pyridazinyl |
| S | O | —CH₂—CH(CCl₃)— | morpholinyl-pyridazinyl |

If 2-chloroethoxy-methoxy-4-chlorobenzene is employed as a compound of the formula (III) and 4-(4-pyridyloxy)phenol as a compound of the formula (II) in Process 2a, the course of the reaction can be described by the following equation:

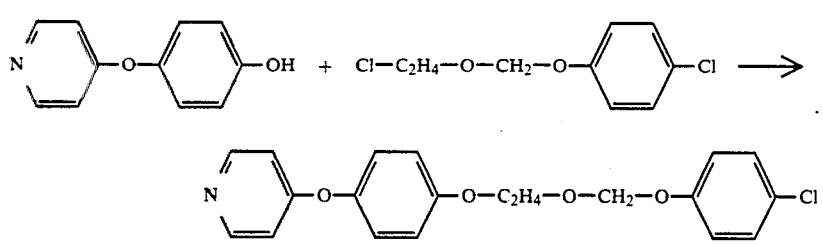

Compounds of the formulae (II) and (III) are preferably employed, in which $R^1$, $R^2$, $R^3$, $R^4$, $R^5$, $R^6$, X, Y, Z, Het, m, n, o and p have the preferred or particularly preferred meanings indicated under the compounds of the formula (I).

The following compounds of the formula (II) may be mentioned in particular:

Het—X—(R¹)—OH

| Het | X | R¹ |
|---|---|---|
| 2-pyridyl | O | H |
| 3-chloro-2-pyridyl | O | H |
| 2-pyridyl | O | 3-Cl |
| 5-chloro-2-pyridyl | O | H |

The following compounds of the formula (III) may be mentioned in particular:

| Hal—M—Y—Z | | | |
|---|---|---|---|
| Hal | M | Y | Z |
| Cl | —CH₂CH₂— | O | 3-pyridyl |

-continued

| Hal | M | Y | Z |
|---|---|---|---|
| Cl | —CH$_2$CH$_2$— | O | 5-chloro-3-methylpyridin-yl |
| Cl | —CH$_2$CH$_2$— | O | 2-methyl-5-(pyridyl with CH$_3$) |
| Br | —CH$_2$CH$_2$— | OCH$_2$ | 3-methylpyridin-yl |
| Br | —CH$_2$CF$_2$— | O | 3-pyridyl |
| Br | —CH$_2$CH$_2$ | O | 2,4-difluorophenyl |
| Br | —CH$_2$CH$_2$CH$_2$— | O | phenyl |

The compounds of the formulae (II) and (III) are known or can be prepared analogously in known processes.

The reaction is carried out by heating the compounds II and III in the presence of diluents and bases.

The reaction is carried out at temperatures of 0°-200° C., preferably at 20°-100° C., particularly preferably at the boiling point of the diluent.

Suitable diluents are all inert organic solvents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, in addition alcohols such as methanol, ethanol, isopropanol and butanol, in addition ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, moreover esters, such methyl acetate and ethyl acetate, in addition nitriles, such as, for example, acetonitrile and propionitrile, benzonitrile, glutaronitrile, moreover amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. Bases which may be mentioned are hydroxides, carbonates, hydrogen carbonates and alkoxides of alkali metals and alkaline earth metals, in addition amines such as, in particular, tertiary amines, for example trimethylamine, triethylamine, N-methylmorpholine, pyridine, picoline, N-ethylpyrrolidine, diazabicyclo(4,3,0)undecane (DBU), 1,4-diazabicyclo(2,2,2)octane (DABCO) and diazabicyclo(3,2,0)nonene (DBN).

The compounds of the formulae II and III are employed in approximately equimolar ratio to one another. An excess of one or the other components conveys no substantial advantage.

After the reaction has taken place, the diluent is removed by distillation and the compounds of the formula I are isolated in a manner known per se by extracting them, for example, from the residue using a suitable solvent, for example ether. The compounds of the formula I can subsequently be purified in a customary manner, for example by distillation.

If 1-methyl-2-[4-(4-pyridyloxy)phenoxy]ethanol is employed as the compound of the formula (IV) and 3-chloropyridine as the compound of the formula (V) in Process 2b for the preparation of the compounds according to the invention, the course of the reaction can be described by the following equation:

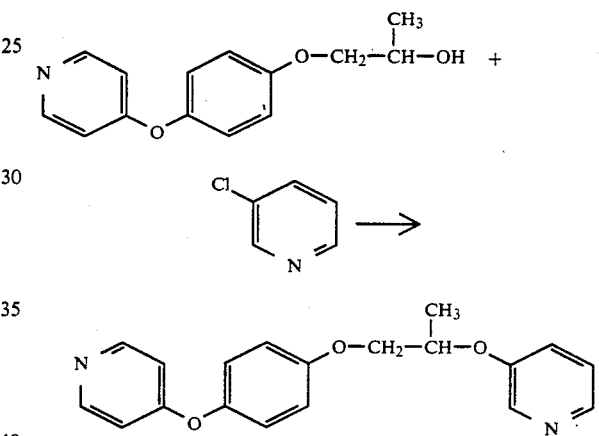

Compounds of the formulae (IV) and (V) are preferably employed, in which R$^1$, R$^2$, R$^3$, R$^4$, R$^5$, R$^6$, X, Y, Z, Het, m, n, o and p have the preferred or particularly preferred meanings indicated in the compounds of the formula (I).

The following compounds of the formula (IV) may be mentioned in particular:

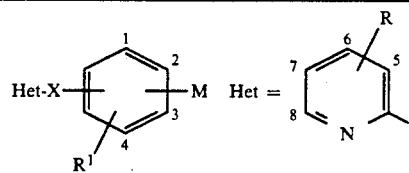

| R[Het] | X | R$^1$ | M |
|---|---|---|---|
| H | CH$_2$ | 1-Cl | 3-O—CH$_2$—CH$_2$—SH |
| 7-Cl | O | H | 2-O—CH$_2$—CH$_2$—SH |
| 7-Cl | O | H | 2-O—CH$_2$—CH$_2$—OH |
| 7-Cl | S | H | 2-O—CH$_2$—CH$_2$—OH |
| H | O | 3-OCH$_3$ | 2-O—CH$_2$—CH(CH$_3$)—OH |
| H | O | 3-OCH$_3$ | 2-O—CH$_2$—CH(CF$_3$)—OH |

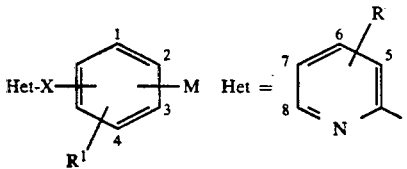

| R[Het] | X | R¹ | M |
|---|---|---|---|
| 7-Cl | CH—CH₃ | H | 2-O—CH₂—CH₂—SH |
| 7-Cl | O | H | 2-O—CH₂—CH(CH₂F)—OH |
| 7-Cl | O | H | 3-O—CH₂—CH(CH₂F)—OH |
| H | S | 3-OCH₃ | 2-O—CH₂—CH(CH₂F)—OH |
| 7-Cl | O | H | 3-O—CH₂—CH(CH₂—OCF₃)—SH |
| 7-Cl | S | H | 2-O—CH₂—CH(CH₂—OCF₃)—OH |
| H | O | 1-Cl, 3-t-Butyl | 2-O—CH(CH₃)—CH₂—OH |

The following compounds of the formula V may be mentioned in particular: 2-chloropyridine, 2-bromopyridine, 2-chloropyrimidine, 2-bromopyrimidine, 3-chloropyridine, 3-bromopyridine, 2-chloro-5-trifluoromethylpyridine, 2-bromo-5-methylpyridine, 4-chloropyridine, 2-chlorobenzothiazole,2-chloropyrazine,2-bromothiazole, 2-chloro-6-methylpyridine, 5-bromopyrimidine, 2-bromothiophene, 3-bromothiophene, 3-chloro-2,5-dimethylpyrazine, 4-chloro-2-methylthiopyrimidine, 2-chlorothiophene, 2,3-dichloropyridine, 2,5-dichloropyridine, 2,6-dichloropyridine, 2,6-dibromopyridine, 3,5-dichloropyridine, 2,4-dichloro-6-methylpyrimidine, 2-4-dichloropyrimidine, 4,6-dichloropyrimidine,2,6-difluoropyridine, 4-6-dichloro-2-methylthiopyrimidine, 2,6-dichloropyrazine, 3,6-dichloropyridazine, 3-chloro-6-N'-alkyl-piperazinyl-pyridazine, 3-chloro-6-dimethyl-morpholinyl-pyridazine, 2-picolyl chloride, 3-picolyl chloride and 4-picolyl chloride.

The compounds of the formulae (IV) and (V) are known (EP-OS 3,877, U.S. Pat. No. 4,491,468).

The reaction is carried out by heating the compounds IV and V in the presence of diluents, bases and optionally catalysts.

The reaction is carried out at temperatures from 0°-200° C., preferably at 20°-100° C., particularly preferably at the boiling point of the diluent.

Suitable diluents are all inert organic solvents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, in addition ethers such as diethylether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, moreover esters, such as methyl acetate and ethyl acetate, in addition nitriles such as, for example, acetonitrile and propionitrile, benzonitrile, glutaronitrile, moreover amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. Hydroxides, carbonates, hydrogencarbonates and alkoxides of alkali metals and alkaline earth metals, in addition amines such as, in particular, tertiary amines, for example trimethylamine, triethylamine, N-methylmorpholine, pyridine, picolines, N-ethylpyrrolidine, diazabicyclo(4,3,0)undecane (DBU), 1,4-diazabicyclo(2,2,2)octane (DABCO) and diazabicyclo(3,2,0)nonene (DBN) may be mentioned as bases.

Suitable catalysts are, for example, phase transfer catalysts such as tris-[2-(2-methoxyethoxy)]-ethylamine (TDA-1), benzyltriethylammonium chloride (TEBA), 1,4,7,10,13,16-hexaoxacyclooctadecane (18-crown-6), tetrabutylammonium bromide, tetrabutylammonium hydrogen sulphate, tetrabutylammonium iodide and methyltrialkyl(C₈-C₁₀) ammonium chloride (Adogen 464).

The compounds of the formulae (IV) and (V) are employed in approximately equimolar ratio to one another. An excess of one or the other components conveys no substantial advantage.

After the reaction has taken place, the diluent is removed by distillation and the compounds of the formula I are isolated in a manner known per se by extracting them, for example, from the residue using a suitable solvent, for example ether. The compounds of the formula I can subsequently be purified in a customary manner, for example by distillation.

If 3-chloropropyloxy-pyridyl phenyl ether is employed as the compound of the formula (VI) and 4-mercaptopyridine as the compound of the formula (VII) in Process 2c for the preparation of the compounds of the formula (I), the course of the reaction can be represented by the following equation:

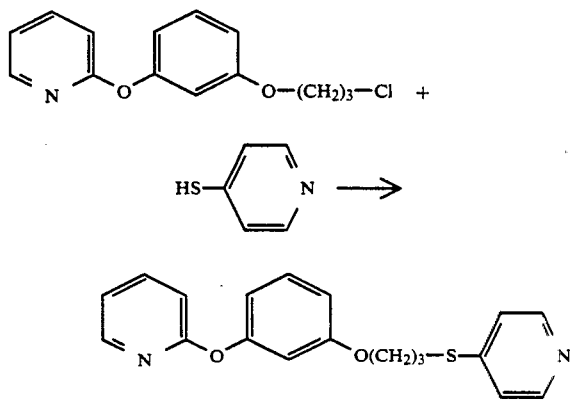

The process is preferably used if the compound of the formula (VII) contains an amino group.

Compounds of the formulae (VI) and (VII) are preferably employed, in which R¹, R², R³, R⁶, X, Y, Z, Het, m, n, o and p have the preferred or particularly preferred meanings indicated in the compounds of the formula (I).

The following compounds of the formula (VI) may be mentioned in particular:

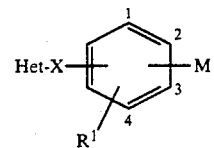

| Het | X | R¹ | M |
|---|---|---|---|
| 2-pyridyl | CH₂ | 1-Cl | 3-O—CH₂—CH₂—Cl |
| 3-chloro-2-pyridyl | O | H | 2-O—CH₂CH₂—Cl |
| 5-trifluoromethyl-2-pyridyl | S | H | 3-O—CH₂CH₂—Cl |
| 6-chloro-2-pyridyl | O | H | 2-O—CH₂CH₂CH₂—Cl |
| 5-trifluoromethyl-2-pyridyl | O | H | 2-O-(2-chlorocyclohexyl) |
| 2-pyridyl | O | H | 3-O-(2-chlorocyclohexyl) |
| 2-pyridyl | O | H | 2-O-(2-chlorocyclopentyl) |
| 2-pyridyl | CH₂ | H | 2-O-(2-chlorocyclopentyl) |
| 2-pyridyl | O | H | 2-O—CH₂CH₂CH₂—Br |
| 2-pyridyl | O | H | 2-O—CH₂—CH(CH₃)—Cl |
| 2-pyrazinyl | O | H | 2-O—CH₂—CH(CH₃)—Cl |
| 2-pyrimidinyl | O | H | 2-O—CH₂—CH(C₂H₅)—Cl |

The following compounds of the formula VII may be mentioned in particular: 2-hydroxypyridine, 2-mercaptopyridine, 2-hydroxypyrimidine, 3-hydroxypyridine, 2-amino-3-hydroxypyridine, 2-chloro-3-hydroxypyridine or 2,3-di-hydorxypyridine.

The compounds of the formulae IVI) and (VII) are known (for example EP-OS 3,877, U.S. Pat. No. 4,491,468).

The reacton is carried out by heating the compounds (VI) and (VII) in the presence of diluents, bases and, if appropriate, catalysts.

The reaction is carried out at temperatures of 0°-200° C., preferably at 20°-100° C., particularly preferably at the boiling point of the diluent.

Suitable diluents are all inert organic solvents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, in addition alcohols such as methanol, ethanol, isopropanol and butanol, in addition ethers such as diethyl ether and dibutyl ether, glycol dimethyl ether, and diglycol dimethyl ether, tetrahydrofuran and dioxane, furthermore ketones, such as acetone, methyl ethyl ketone, methyl isopropyl ketone and methyl isobutyl ketone, moreover esters, such methyl acetate and ethyl acetate, in addition nitriles, such as, for example, acetonitrile and propionitrile, benzonitrile, glutaronitrile, moreover amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. Bases which may be mentioned are hydroxides, carbonates, hydrogen carbonates and alkoxides of alkali metals and alkaline earth metals, in addition amines such as, in particular, tertiary amines, for example trimethylamine, triethylamine, N-methylmorpholine, pyridine, picolines, N-ethylpyrrolidine, diazabicyclo(4,3,0)-undecane (DBU), 1,4-diazabicyclo(2,2,2)octane (DABCO) and diazabicyclo(3,2,0)nonene (DBN).

Suitable catalysts are, for example, phase transfer catalysts such as methyltrialkyl(C₈-C₁₀)-ammonium chloride (Adogen 464), 1,4,7,10,13,16-hexaoxacyclooctadecane (18-crown-6), tetrabutylammonium bromide, tris-[2-(2-methoxyethoxy)-ethyl]-amine (TDA-1) and benzyltriethylammonium chloride (TEBA).

The compounds of the formulae (VI) and (VII) are employed in approximately equimolar ratio to one another. An excess of one or the other components conveys no substantial advantage.

After the reaction has taken place, the diluent is removed by distillation and the compounds of the formula I are isolated in a manner known per se by, for example, extracting them from the residue using a suitable solvent, for example ether. The compounds of the formula (I) can subsequently be purified in a customary manner, for example by distillation.

If 1-methyl-1-(3-hydroxyphenoxy)ethanol is employed as the compound of the formula (VIII) and 2-chloropyridine as the heterocyclic compound in Process 2d, the course of the reaction can be represented by the following equation:

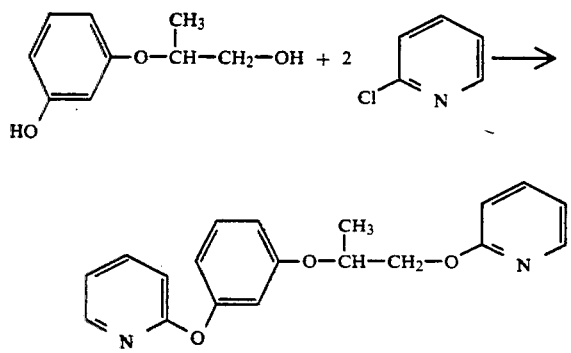

Compounds of the formulae (VIII) and (IX) are preferably employed, in which $R^1$–$R^6$, Het, X, Y, Z, m, n, o, and p have the preferred and particularly preferred meanings indicated in the compounds of the formula (I).

The compounds of the formulae (VIII) and (IX) are known or can be prepared analogously by known processes.

The reaction is carried out as described in Process 2b.

The active compounds are suitable for combating animal pests such as arthropods, preferably insects and arachnida, which occur in animal keeping and animal rearing with household and productive animals and also with zoo, laboratory, experimental and pet animals, and have favorable toxicity to warm-blooded animals. They are active against all or individual stages of development of the pests and also against resistant and normally sensitive species of the pests.

By combating the animal pests, diseases and their transmission, cases of death and yield reductions (for example in the production of meat, milk, wool, hides, eggs) should be prevented so that more economical and simpler animal keeping is possible or, in certain areas, is only possible by the use of the active compounds.

The pests include:
from the order of the Anoplura, for example, Haematopinus spp., Linognathus spp., Solenopotes spp., Pediculus spp. and Pthirus spp.;
from the order of the Mallophaga, for example, Trimenopon spp., Menopon spp., Eomenacanthus spp., Menacanthus spp., Trichodectes spp., Felicola spp., Damalinea spp. and Bovicola spp.;
from the order of Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.;
from the order of Siphonaptera, for example, Ctenocephalides spp., Echidnophaga spp., Ceratophyllus spp.;
from the order of Metastigmata, for example, Hyalomma spp., Rhipicephalus spp., Boophilus spp., Amblyomma spp., Haemophysalis spp., Dermacentor spp., Ixodes spp., Argas spp., Ornithodorus spp., Otobius spp.;
from the order of Mesastigmata, for example, Dermanyssus spp., Ornithonyssus spp., Pneumonyssus spp.;
from the order of Prostigmata, for example, Cheyletiella spp., Psorergates spp., Myobia spp., Demodex spp., Neotrombicula spp.;
from the order of Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp., Lytodites spp., Laminosioptes spp..

The household and productive animals include mammals such as, for example, cattle, sheep, goats, horses, pigs, dogs, cats, camels, water buffalo, donkeys, rabbits, fallow deer, reindeer, animals with valuable fur such as, for example, mink, chinchilla, racoon, birds such as, for example, hens, turkeys, pheasants, geese and ducks.

The laboratory and experimental animals include, for example, mice, rats, guinea pigs, golden hamsters, dogs and cats.

The pet animals include, for example, dogs and cats.

Administration can be carried out both prophylactically and therapeutically.

The administration of the active compounds is carried out directly, or enterally, parenterally, dermally or nasally in the form of suitable preparations, by the treatment of the environment or with the aid of active compound-containing molded articles such as, for example, strips, sheets, tapes, neckbands, ear tags, limb bands and labelling devices.

Enteral administration of the active compounds takes place, for example, orally in the form of powders, tablets, capsules, pastes, boli, drinks, granules, orally administrable solutions, suspensions or emulsions, medicated feed or drinking water. Dermal administration takes place, for example, in the form of dipping, spraying or pouring on and spotting on and powdering. Parenteral administration takes place, for example, in the form of injection (for example intramuscular, subcutaneous, intravenous) or by implants.

Preparations for dermal administration are to be emphasized particularly. These include solutions, suspension and emulsion concentrates and microemulsions which are diluted with water before use, pour-on and spotting-on formulations, powders and dusts, aerosols and active compound-containing molded articles as well as dust-bags and back-rubbers.

These preparations are prepared in a known manner, for example by mixing the active compound with extenders, i.e., for example, liquid solvents, optionally using surface-active agents, i.e. emulsifiers and/or dispersants. In the case of the use of water as an extender, for example, organic solvents may also be used as auxiliary solvents.

In addition to water, the liquid diluents include alcohols such as methanol, ethanol, isopropanol, n-butanol, amyl alcohol and octanol; glycols such as propylene glycol, 1,3-butylene glycol, ethyl glycol and dipropylene glycol monomethyl ether; glycerol; aromatic alcohols such as benzyl alcohol; carboxylic acid esters such as, for example, ethyl acetate, benzylbenzoate, butyl acetate, propylene carbonate, ethyl lactate; aliphatic hydrocarbons such as paraffins, cyclohexane, methylene chloride, ethylene chloride; aromatic hydrocarbons such as xylene, toluene, alkyl-naphthalenes, chlorobenzenes; ketones such as, for example, acetone and methyl ethyl ketone, methyl isobutyl ketone, cyclohexanone; natural and synthetic mono-and triglycerides containing natural fatty acids such as cottonseed oil, ground nut oil, maize germ oil, olive oil, castor oil and sesame oil; furthermore dimethyl sulphoxide, dimethylacetamide, dimethylformamide, N-methylpyrrolidone, dioxane and 2,2-dimethyl-4-hydroxymethyl-1,3-dioxolane.

The surface-active substances include: emulsifiers and wetting agents such as anion-active surfactants, for example alkylsulphonates, alkyl sulphates, arylsulphonates, Na lauryl-sulphates, fatty alcohol ether sulphates, mono/dialkylpolyglycol ether orthophosphoric acid ester monoethanolamine salt, calcium alkylarylsulphonate; cation-active surfactants, for example cetyltrimethylammonium chloride; ampholytic surfactants, for example di-Na N-lauryl-betaiminodipropionate or lecithin; non-ionic surfactants, for example polyoxyethylated castor oil, polyoxyethylated sorbitan monooleate, polyoxyethylated sorbitan monostearate, glycerol monostearate, polyoxyethylene stearate, alkylphenol polyglycol ethers, polyoxyethylated sorbitan monopalmitate, polyoxyethylene lauryl ether, polyoxyethylene oleyl ether, polyoxyethylene mannitan monolaurate, alkyl polyglycol ethers, oleyl polyglycol ether, dodecyl polyglycol ether, ethoxylated nonylphenol and isooctylphenylpolyoxyethanol.

The preparations may additionally contain: adhesives, for example carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, paraffins, oils, waxes, hydrogenated castor oil, lecithins and synthetic phospholipids.

The preparations may contain colorants such as inorganic pigments, for example iron oxide, titanium oxide, Prussian blue and organic dyes, such as alizarin, azo dyes and metal phthalocyanine dyes.

The preparations may contain disintegrants, for example silicone oils of different viscosity, fatty acid esters such as ethyl stearate, di-n-butyl adipate, hexyl laurate, dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxlike fatty acid esters, dibutyl phthalate, diisopropyl adipate, ester mixtures related to the latter, etc.; triglycerides such as caprylic/capric acid triglyceride, triglyceride mixtures containing plant fatty acids of chain length $C_8$-$C_{12}$ or other specifically selected natural fatty acids, partial glyceride mixtures of saturated or unsaturated fatty acids, possibly also containing hydroxyl groups, monodiglycerides of $C_8$/$C_{10}$ fatty acids and others; fatty alcohols such as isotridecyl alcohol, 2-octyldodecanol, cetylstearyl alcohol and oleyl alcohol.

In order to produce solid preparations, the active compound is mixed with suitable excipients, if appropriate with the addition of auxiliaries, and brought into the desired form.

Excipients which may be mentioned are all physiologically compatible solid inert substances. Inorganic and organic substances are used as such. Inorganic substances are optionally crushed and fractionated, for example synthetic and natural ground minerals such as kaolins, talc, chalk, quartz, diatomaceous earth, rock salt, carbonates such as calcium carbonate, hydrogen carbonates, aluminum oxides, silicic acids, aluminas, precipitated or colloidal silica and phosphates.

Organic substances are, for example, sugar, cellulose, foodstuffs and feedstuffs such as milk powder, animal meals, cereal meals and shreds, starches and sawdust.

Auxiliaries are preservatives, antioxidants, and colorants, which have already been mentioned above.

Other suitable auxiliaries are lubricants and glidants such as, for example, magnesium stearate, stearic acid, talc, bentonites, disintegration-promoting substances such as starch or cross-linked polyvinylpyrrolidone, binders such as, for example, starch, gelatine or linear polyvinylpyrrolidone and dry binders such as microcrystalline cellulose.

The active compounds in the form of their solid or liquid formulations mentioned above can also be present as capsules.

The active compounds can also be used in the form of an aerosol. For this purpose, the active compound is finely dispersed in a suitable formulation under pressure.

It may also be advantageous to use the active compounds in formulations which release the active compound in a sustained manner. Those which may be mentioned are active compound-containing molded articles such as, for example, sheets, tapes, strips, neckbands, ear tags, tail tags, limb bands, halters and marking devices. Active compound-containing implants and boli may also be mentioned.

The administration of the active compounds can also be carried out together with the feed and/or the drinking water.

The active compounds can be present in the formulations alone or in a mixture with other active compounds or synergists.

Directly administered formulations contain between $10^{-7}$ and 5% by weight, preferably between $10^{-4}$ and 1% by weight of active compound.

Formulations which are only administered after further dilution contain 1-95% by weight, preferably 5-90% by weight of active compound.

FORMULATION EXAMPLES

1. Preparation of an emulsion concentrate

| | |
|---|---|
| (a) Active compound according to Example 1 (100%) | 25.00 g |
| non-ionic emulsifier (emulsifier 368 ® = alkylaryl polyglycol ether MW about 1165) | 25.00 g |
| Dipropylene glycol monomethyl ether to | 100.00 ml |

Preparation

The substances are weighed together and stirred until a clear solution is formed.

Before use, the solution is diluted to its use

| (b) Active compound according to Example 2 (100%) | 1.00 g |
|---|---|
| polyoxyethylene stearate | 0.50 g |
| sorbitan sesquioleate | 0.40 g |
| water | 4.00 g |
| polyethylene glycol | 200 to 100 ml |

2. Preparation of a pour-on formulation

| (a) Composition | |
|---|---|
| Active compound according to Example 1 (100%) | 5.00 g |
| isopropyl myristate | 30.00 g |
| 2-octyldodecanol | 20.00 g |
| isopropanol to | 100 ml |

Preparation:

The substances are weighed together and stirred until a clear solution results.

| (b) Composition | |
|---|---|
| Active compound according to Example 1 (100%) | 0.50 g |
| silicone oil 100 | 30.00 g |
| butyl acetate to | 100 ml |

3. Preparation of a microemulsion

| Active compound according to Example 1 (100%) | 13.00 g |
|---|---|
| Eumulgin B3 ® (alkylaryl polyglycol ether) | 30.00 g |
| Cetiol HE ® (polyol fatty acid ester) | 30.00 g |
| isopropyl myristate | 5.00 g |
| benzyl alcohol | 3.00 g |
| water to | 100 ml |

Preparation:

The active compound is dispersed in the lipophilic components (Eumulgin, Cetiol, benzyl alcohol, isopropyl myristate).

After warming to 60° C., water of the same temperature is admixed and the mixture is cooled. The resultant microemulsion is superficially similar to a clear solution.

Preparation of a spray formulation

| Composition | |
|---|---|
| Active compound according to Example 1 (100%) | 20 g |
| Toximul ® emulsifier (mixture of Ca alkylbenzenesulphonate and non-ionogenic emulsifiers and methanol) | 7 g |
| Toximul S ® emulsifier (mixture of Ca alkylbenzenesulphonate and non-ionogenic emulsifier and | 5 g |

| -continued | |
|---|---|
| Composition | |
| methanol) | |
| Sovesso 200 ® (alkylnaphthalene mixture of high-boiling mineral oil fractions) | to 100 ml |

Preparation:

The active compound is weighed together with the residual components, stirred and diluted with water to the administration concentration before use.

USE EXAMPLES

A. In vitro test on fleas (all stages of development)

Test object: all stages (eggs, larvae, pupae, adults) of *Ctenocephalides felis*

Test procedure

The substance to be tested is distributed homogeneously in dried blood in the concentration desired. Flea eggs, which have been collected from flea-infested cats, are added to this mixture of dried blood and test substance and incubated at 80% relative humidity and 25° C.

After expiry of the development time of 3 to 4 weeks, it is determined whether adult fleas have developed. A 100% action here means that no adult fleas have been determined and 0% that living adult fleas have been determined.

The active compound according to Example 1 shows 100% action at 5 ppm.

B. In vivo test on fleas (all stages of development)

Test object: eggs, larvae, and pupae, of *Ctenocephalides felis* in the environment of dogs/cats, adult fleas on dogs/cats.

Test procedure

Beds of flealess dogs/cats in boxes are sprayed with the substance to be tested in the use concentration desired. At determined times after the administration, eggs of Ctenocephalides felis, which had been collected from infested cats, are added to the beds of the dogs/cats. It is determined whether and at which point in time the dogs/cats situated in the boxes are infested by adult fleas.

A 100% action here means that the dogs/cats have no flea infestation and 0% action that the dogs/cats are infested by fleas.

The active compound according to Example 1 shows 100% action.

Preparation Examples for Process 2a

General procedure

A mixture of 1 mol of the compound of the formula (II) and the approximately 1.1- to 2-fold molar amount of compound of the formula (III) and the approximately 1-to 4-fold molar amount of $K_2CO_3$ powder are heated to reflux in acetonitrile for about 24 hours. After cooling, the solution is filtered off from the salts and the filtrate is concentrated in vacuo. The resultant product is purified further by bulb tube distillation, recrystallization or column chromatography.

The following compounds are obtained according to this procedure.

| Ex. No. | Het | X | R¹ₘ (phenyl) | [O(C)ₙ(C)ₙ Y]ₚ | Z | B.P. (°C./pressure) or M.P. °C. |
|---|---|---|---|---|---|---|
| 1 | 2-pyridyl | O | p-phenylene | —O—CH₂CH₂—O— | 3-pyridyl | 210–230° C./0.4 mm |
| 2 | 2-pyridyl | O | p-phenylene | —O—CH₂CH₂CH₂—O— | 3-pyridyl | 220–240° C./0.4 mm |
| 3 | 3-CF₃-2-pyridyl | O | p-phenylene | —O—CH₂CH₂CH₂—O— | 3-pyridyl | 240–250° C./0.3 mm |
| 4 | 2-(methylthio)benzothiazolyl-type | O | p-phenylene | —O—CH₂CH₂CH₂—O— | 5-chloro-3-pyridyl | 230–240° C./0.1 mm |
| 5 | 2-pyridyl | O | p-phenylene | —O—CH₂CH₂—O— | 2-amino-3-pyridyl | 230–240° C./0.1 mm |
| 6 | 2-pyridyl | O | p-phenylene | —O—CH₂CH₂—O— | phenyl | 98° C. |
| 7 | 2-pyrazinyl | O | p-phenylene | —O—CH₂CH₂—O— | 4-fluorophenyl | 220–240° C./0.3 mm |

-continued

| Ex. No. | Het | X | (R¹)m ring | $-[O-(C)_n-(C)_n-Y-]_p$ | Z | B.P. (°C./pressure) or M.P. °C. |
|---|---|---|---|---|---|---|
| 8 | 4-CF₃-pyridin-2-yl | O | phenylene | —O—CH₂CH₂—O— | 4-F-phenyl | 65° C. |
| 9 | pyridin-2-yl | O | phenylene | —OCH₂CH₂—O— | 4-F-phenyl | 92° C. |
| 10 | pyridin-2-yl | O | phenylene | —O—CH₂CH₂—O— | 2,4-Cl₂-phenyl | 128° C. |
| 11 | pyrazin-2-yl | O | phenylene | —OCH₂CH₂—O— | phenyl | 210–235° C./0.3 mm |
| 12 | 2-(methylthio)benzothiazol-type | O | phenylene | —OCH₂CH₂—O— | phenyl | 240° C./0.3 mm |
| 13 | pyrimidin-2-yl | O | phenylene | —OCH₂CH₂—O— | phenyl | 105° C. |
| 14 | 4-CF₃-pyridin-2-yl | O | phenylene | —OCH₂CH₂—S— | phenyl | 230° C./0.3 mm |

-continued

| Ex. No. | Het | X | $R^1_m$ | $-[O-(C)_n-(C)_n-Y-]_p-$ | Z | B.P. (°C./pressure) or M.P. °C. |
|---|---|---|---|---|---|---|
| 15 | F$_3$C-pyridine-CH$_3$ | O | phenyl | —OCH$_2$CH$_2$—O— | phenyl | 210-225° C. 0.3 mm |
| 16 | pyridine-CH$_3$ | O | phenyl | —OCH$_2$CH$_2$—O— | 4-Cl, 1-OCF$_3$ phenyl | 125-128° C. |
| 17 | pyrazine-CH$_3$ | O | phenyl | —OCH$_2$CH$_2$—O— | pyridine | 113-115° C. |
| 18 | Cl, CH$_3$, F$_3$C-pyridine | O | phenyl | —OCH$_2$CH$_2$—O— | 2-OCH$_3$ phenyl | 121-123° C. |
| 19 | pyridine-CH$_3$ | O | phenyl | —O—CH$_2$CH$_2$—O— | Cl-pyridine | 53° C. |
| 20 | pyrazine-CH$_3$ | O | phenyl | —OCH$_2$CH$_2$—O— | Cl-pyridine | 93° C. |

-continued

| Ex. No. | Het | X | ⟨R¹m phenyl⟩ | -O-(C)n-(C-C)p-Y- | Z | B.P. (°C./pressure) or M.P. °C. |
|---|---|---|---|---|---|---|
| 21 | pyrimidine (2-methyl) | O | phenyl | —OCH$_2$CH$_2$—O— | 3-chloro-5-methylpyridine | 104° C. |
| 22 | 3-chloro-2-methylpyridine | O | phenyl | —OCH$_2$CH$_2$CH$_2$—O— | 3-chloro-5-methylpyridine | 240° C./0.1 mm |
| 23 | 2-methylpyridine | O | phenyl | —OCH$_2$CH$_2$CH$_2$—O— | 3-chloro-5-methylpyridine | 58° C. |
| 24 | 2-methylpyridine | O | phenyl | —OCH$_2$CH$_2$CH$_2$—O— | 2-CH$_3$-5-methylpyridine | 230° C./0.3 mm |
| 25 | 2-methylpyrazine | O | phenyl | —OCH$_2$CH$_2$—S— | phenyl | 220° C./0.4 mm |
| 26 | 3-chloro-2-methylpyridine | O | phenyl | —OCH$_2$CH$_2$—S— | phenyl | 240° C./0.2 mm |

-continued

| Ex. No. | Het | X | ⟨phenyl⟩-R¹ₘ | $[O(C)_n-(C-C)_n-Y]_p$ | Z | B.P. (°C./pressure) or M.P. °C. |
|---|---|---|---|---|---|---|
| 27 | pyrimidin-2-yl | O | phenyl | —OCH₂O— | 4-Cl-phenyl | 230° C./0.3 mm |
| 28 | pyrimidin-2-yl | O | phenyl | —OCH₂CH₂—S— | phenyl | 230° C./0.4 mm |
| 29 | 6-methylpyridin-2-yl | O | phenyl | —OCH₂O— | 4-Cl-phenyl | 210° C./0.4 mm |
| 30 | 6-(H₃C—O—C(=O))-pyridin-2-yl | O | phenyl | —OCH₂CH₂—O— | phenyl | 240° C./0.2 mm |
| 31 | pyrimidin-2-yl | O | phenyl | —OCH₂O— | 4-Cl-phenyl | 220–240° C./0.4 mm |
| 32 | 6-methylpyridin-2-yl | O | phenyl | —O—CH₂CF₂—O— | pyridinyl | 240° C./0.2 mm |
| 33 | 6-methylpyridin-2-yl | O | phenyl | —O—CH₂CF₂—O— | Cl-pyridinyl | 240–250° C./0.1 mm |

-continued

| Ex. No. | Het | X | $\phantom{X}$R$^1_m$ phenyl | $[O(C)_n(C-C)_o-Y]_p$ | Z | B.P. (°C./pressure) or M.P. °C. |
|---|---|---|---|---|---|---|
| 33a | 2-(CH$_2$CH$_2$CH$_2$CH$_3$)-benzofuran | =N—OCH$_3$ (—C=) | phenyl | —O—CH$_2$CH$_2$—O— | phenyl | 250° C./0.1 mm |
| 33b | 2-methylpyridine | O | phenyl | —O—CH$_2$CH$_2$—O— | 2-chloro-3-methylpyridine | 91–92° C. |
| 33c | 2,6-dimethyl-4-methylpyrimidine | S | phenyl | —O—CH$_2$CH$_2$CH$_2$—O— | 5-chloro-3-methylpyridine | 240° C./0.1 mm |
| 33d | 2,6-dimethyl-4-methylpyrimidine | S | phenyl | —O—CH$_2$CH$_2$—O— | 5-chloro-3-methylpyridine | 230° C./0.1 mm |

Preparation Examples for Process 2b

General procedure

A mixture of 1 mol of the compound of the formula (IV) and the approximately 1.1- to 3-fold molar amount of compound of the formula (V), the approximately 4-fold molar amount of NaOH powder, the approximately 1.1-fold molar amount of $K_2CO_3$ powder and the approximately 0.02-fold amount of the phase transfer catalyst tris-(2-(2-methoxyethoxy)-ethyl)-amine are heated to reflux in toluene for about 36 hours. After cooling, the toluene phase is washed with water, dried over $Na_2SO_4$ and concentrated in vacuo. The resultant product is purified further by bulb tube distillation, recrystallization or column chromatography.

The following compounds are obtained according to this procedure.

| Ex. No. | Het | X | 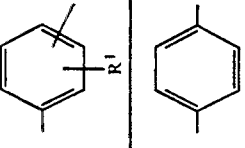 R¹ | —O—(—C—)ₙ—(C—C)ₘ—Y— | Z | B.P. (°C./pressure) or M.P. °C. |
|---|---|---|---|---|---|---|
| 34 |  | O | 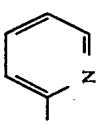 | —O—CH₂—CH—O— <br> \|<br>CH₃ | 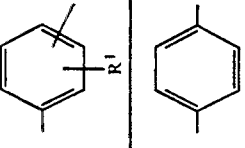 | 210–230° C./0.4 mm 56° C. |
| 35 |  | O | 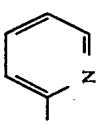 | —O—CH—CH₂—O— <br> \|<br>CH₃ | 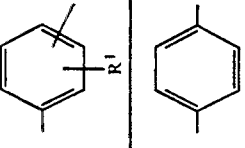 | 215–235° C./0.4 mm 76° C. |
| 36 |  | O | 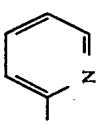 | —O—CH₂CH₂—O— | 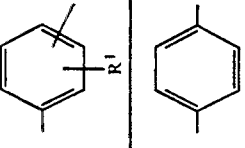 | 205–225° C./0.4 mm |
| 37 |  | O | 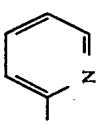 | —O—CH₂—CH—O— <br> \|<br>CF₃ | 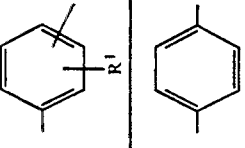 | 220–240° C./0.4 mm |
| 38 |  | O | 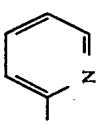 | —O—CH₂—CH—O— <br> \|<br>CH₃ | 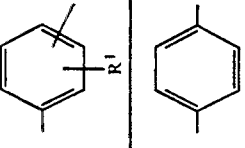 | 230° C./0.4 mm |
| 39 |  | O | 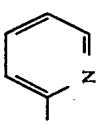 | —O—CH—CH₂—O— <br> \|<br>CH₃ | 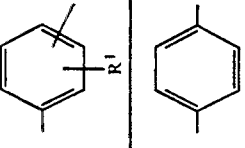 | 230° C./0.4 mm |
| 40 |  | —CH₂— | 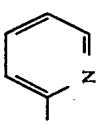 | —O—CH₂CH—O— <br> \|<br>CH₃ |  | 235° C./0.4 mm |

-continued

| Ex. No. | Het | X | [benzene with R¹] | $\pm O \pm C_n \pm (C - C)_{np} Y -$ | Z | B.P. (°C./pressure) or M.P. °C. |
|---|---|---|---|---|---|---|
| 41 | pyridyl | —CH₂— | phenyl | —O—CH—CH₂—O—<br>　　　│<br>　　CH₃ | pyridyl | 230° C./0.4 mm |
| 42 | pyridyl | —O— | phenyl | —O—CH₂CH—O—<br>　　　　│<br>　　　CH₃ | pyridyl | 230° C./0.4 mm |
| 43 | pyrimidyl | —O— | phenyl | —O—CH₂—CH—O—<br>　　　　　│<br>　　　　CH₃ | pyridyl | 235° C./0.4 mm |
| 44 | pyridyl | —O— | phenyl | —O—CH₂CH—O—<br>　　　　│<br>　　　CH₃ | pyridyl | yellow wax |
| 45 | pyridyl | —O— | phenyl | —O—CH₂CH₂—O—CH₂—<br>　　　　　　　　│<br>　　　　　　　CH₃ | pyridyl | 240–250° C./0.4 mm |
| 46 | 5-Cl-pyridyl | O | phenyl | —O—CH₂CH₂—O—CH₂CH₂—O— | pyridyl | 220–230° C./0.2 mm |
| 47 | pyridyl | O | phenyl | [cyclohexane-1,2-diyl dioxy] | pyridyl | 230° C./0.3 mm |

-continued

| Ex. No. | Het | X | R¹ (phenyl) | $-(O)_n-(C-C)_{m/p}-Y-$ | Z | B.P. (°C./pressure) or M.P. °C. |
|---|---|---|---|---|---|---|
| 48 | 3-Cl-2-methylpyridyl | —O— | phenyl (1,4) | —O—CH$_2$CH(CH$_3$)—O— | 2-pyridyl | 230° C./0.3 mm |
| 49 | 3-Cl-2-methylpyridyl | —O— | phenyl (1,4) | —O—CH$_2$CH(CH$_3$)—O— | 5-Cl-2-pyridyl | 240° C./0.2 mm |
| 50 | 2-methylpyridyl | —O— | phenyl (1,4) | —O—CH$_2$CH(CH$_3$)—O— | 3-Cl-2-pyridyl | 225° C. 0.4 mm |
| 51 | 2-methylpyridyl | —O— | phenyl (1,4) | —O—CH$_2$CH(CH$_3$)—O— | 6-OCH$_3$-2-pyridyl | 240/0.3 mm |
| 52 | 2-methylpyridyl | O | phenyl (1,4) | —O—CH$_2$CH(CH$_3$)—O— | 5-Cl-2-pyridyl | 230° C./0.4 mm |
| 53 | 2-methylpyridyl | O | phenyl (1,4) | —O—CH$_2$CH(CH$_3$)—O— | 3-CF$_3$-5-Cl-2-pyridyl | 230–250° C./0.3 mm |

-continued
| Ex. No. | Het | X | 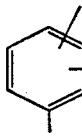 | $+O(C)_n$—$(C—C)_mp$—Y— | Z | B.P. (°C./pressure) or M.P. °C. |
|---|---|---|---|---|---|---|
| 54 |  | O | 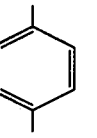 | —O—CH$_2$CH—O—<br>          \|<br>          CH$_3$ |  | 230° C./0.1 mm |
| 55 | 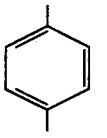 | O |  | —O—CH$_2$CH—O—<br>          \|<br>          CH$_3$ | 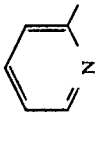 | 240/0.4 mm |
| 56 | 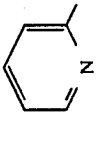 | O | 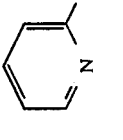 | —O—CH$_2$CH—O—<br>          \|<br>          CH$_3$ | 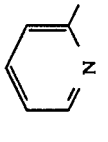 | 230° C./0.4 mm |
| 57 | 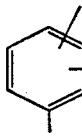 | O |  | —O—CH$_2$CH—O—<br>          \|<br>          CH$_3$ | 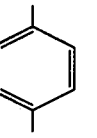 | 240° C./0.2 mm |
| 58 |  | O | 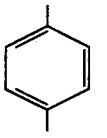 | 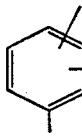 |  | 230° C./0.3 mm |
| 59 | 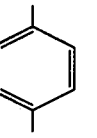 | O |  | 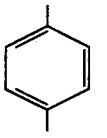 | 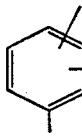 | 230–250° C./0.2 mm |

-continued

| Ex. No. | Het | X | R¹ | $-\text{+O+C}_n-(C-C_m)_p-Y-$ | Z | B.P. (°C./pressure) or M.P. °C. |
|---|---|---|---|---|---|---|
| 60 | 2-methylpyridine | O | 2,6-dimethylphenyl | —O—CH₂CH(CH₃)—O— | 2-methylpyridine | 240° C./0.2 mm |
| 61 | 2-methylpyridine | O | 2,6-dimethylphenyl | —O—CH₂CH(CH₃)—O— | 5-chloro-2-methylpyridine | 240–250° C./0.2 mm |
| 62 | 4-chloro-2-methylpyridine | O | phenyl | —O—CH₂CH(CH₃)—O— | 2-methylpyridine | 230/0.3 mm |
| 63 | 2-methylpyridine | O | phenyl | 1,2-dimethoxycyclohexane linkage | 5-chloro-2-methylpyridine | 240° C./0.2 mm |
| 64 | 2-methylpyridine | O | phenyl | —O—CH₂CH(CH₂CH₃)—O— | 2-methylpyridine | 220° C./0.3 mm |
| 65 | 2-methylpyridine | O | phenyl | —O—CH₂CH(CH₂CH₃)—O— | 3-chloro-2-methylpyridine | 230° C./0.3 mm |

-continued

| Ex. No. | Het | X | R¹ | $-\text{O}(\text{C})_n-(\text{C}-\text{C})_p-Y-$ | Z | B.P. (°C./pressure) or M.P. °C. |
|---|---|---|---|---|---|---|
| 66 | 6-methoxy-2-pyridyl | O | 1,4-phenylene | —O—CH₂CH—O— | 2-pyridyl (6-methyl) | 220–240° C./0.3 mm |
| 67 | 6-methoxy-2-pyridyl | O | 1,4-phenylene | —O—CH₂CH—O—<br>　　　　CH₃ | 5-chloro-2-pyridyl (6-methyl) | 230–250° C./0.25 mm |
| 68 | 2-pyridyl (6-methyl) | O | 1,4-phenylene | —O—CH—CH—O—<br>　　CH₃ CH₃ | 2-pyridyl (6-methyl) | 220–240° C./0.3 mm |
| 69 | 2-pyridyl (6-methyl) | O | 1,4-phenylene | —O—CH—CH—O—<br>　　CH₃ CH₃ | 3-chloro-2-pyridyl (6-methyl) | 250° C./0.3 mm |
| 70 | 2-pyridyl (6-methyl) | O | 1,4-phenylene | —O—CH₂CH—O—<br>　　　CH₂—O—CH₂—CH=CH₂ | 2-pyridyl (6-methyl) | 240° C./0.2 mm |
| 71 | 2-pyridyl (6-methyl) | O | 1,4-phenylene | —O—CH₂CH—O—<br>　　　　CH₃ | 2-fluoro-6-methyl-pyridyl | 240° C./0.3 mm |
| 72 | 2-pyridyl (6-methyl) | O | 1,4-phenylene | —O—CH₂CH₂—O—<br>CH₂CH₂—O—CH₂CH₂—O—<br>CH₂CH₂O— | 2-pyridyl (6-methyl) | 240° C./0.1 mm |

-continued

| Ex. No. | Het | X | $\left(\text{phenyl-}R^1\right)$ | $+O+C)_n-(C-C)_p-Y-$ | Z | B.P. (°C./pressure) or M.P. °C. |
|---|---|---|---|---|---|---|
| 73 | 2-methylpyridine | O | phenyl | —O—CH₂CH₂—O—CH₂CH₂—O— | 2-pyridyl | 240° C./0.2 mm |
| 74 | 2-methylpyridine | O | phenyl | —O—CH₂CH—O—<br>　　　　CH₂—O—CH₃ | 3-chloro-2-pyridyl | 38-40° C. |
| 75 | 4-methyl-2-chloro-3-methoxyphenyl | O | phenyl | —O—CH₂CH—O—CH₂CH—O—<br>　　　　CH₃　　　　CH₃ | 2-pyridyl | 250° C./0.2 mm |
| 76 | 3-methylpyridine | O | phenyl | —O—CH₂CH—O—<br>　　　　CH₃ | 2-pyridyl | 230° C./0.2 mm |
| 77 | 4-methylpyridine | CH₂ | phenyl | —O—CH₂CH—O—<br>　　　　CH₃ | 2-pyridyl | 240° C./0.3 mm |
| 78 | 2-methylpyridine | O | phenyl | —O—CH₂CH—O—CH₃<br>　　　　CH₃ | 2-methylthienyl | 220° C./0.25 mm |
| 79 | 2-methylpyridine | —CH₂O— | phenyl | —O—CH₂CH—O—CH₃<br>　　　　CH₃ | 2-pyridyl | 230° C./0.3 mm |

-continued

| Ex. No. | Het | X | R¹ | $-O-(-CH_2-)_n-(C-)_m-Y-$ | Z | B.P. (°C./pressure) or M.P. °C. |
|---|---|---|---|---|---|---|
| 80 | 2-methyl-6-chloropyridin-3-yl | O | phenyl | $-O-CH_2CH-O-CH_2-O-CH_3$ | 2-methylthiophen-5-yl | 230–240° C./0.2 mm |
| 81 | 2-methylpyridin-3-yl | O | phenyl | $-O-CH_2CH-O-CH_2-O-CH_3$ | benzothiazol-2-yl | 250° C./0.1 mm |
| 82 | 2-methylpyridin-3-yl | O | phenyl | $-O-CH_2CH-O-CH_2-CH=CH_2$ | benzothiazol-2-yl | 250° C./0.1 mm |
| 83 | 2-methylpyridin-3-yl | O | phenyl | $-O-CH_2CH-O-CH_2-CH=CH_2$ | 2-methyl-6-fluoropyridin-3-yl | 240° C./0.2 mm |
| 84 | 2-butylbenzofuran-3-yl | C=N-OCH₃ | phenyl | $-O-CH_2CH-O-CH_3$ | 2-methylpyridin-3-yl | 250° C./0.1 mm |
| 85 | 2-butylbenzofuran-3-yl | C=N-OCH₃ | phenyl | $-O-CH_2CH-O-CH_3$ | 2-methyl-5-chloropyridin-3-yl | 250° C./0.1 mm |

-continued
| Ex. No. | Het | X | 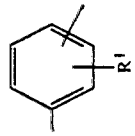 | $\mathrm{+O+C)_n-(C-C)_p}Y-$ | Z | B.P. (°C./pressure) or M.P. °C. |
|---|---|---|---|---|---|---|
| 86 | 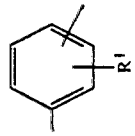 | S | 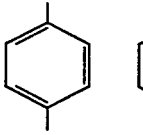 | —O—CH₂CH—O— <br>     CH₃ | 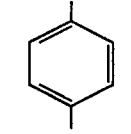 | 240° C./0.1 mm |
| 87 | 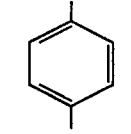 | O | 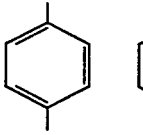 | —O—CH₂CH—O— <br>     CH₃ | 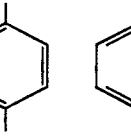 | 240° C./0.2 mm |
| 88 | 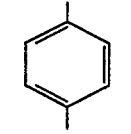 | O | 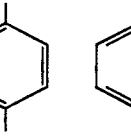 | —O—CH₂CH—O— <br>     CH₃ | 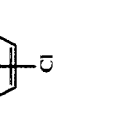 | 240° C./0.2 mm |
| 89 | 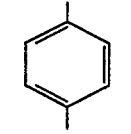 | O | 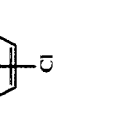 | —O—CH₂CH—O— <br>     CH₃ | | 235° C./0.2 mm |
| 90 | | O | | —O—CH₂CH—O—CH₂CH—O—CH₂CH—O <br>     CH₃    CH₃    CH₃ | | 250° C./0.1 mm |
| 91 | | O | | —O—CH₂CH—O— <br>     CH₃ | | 240° C./0.1 mm |

-continued

| Ex. No. | Het | X | (R¹ aryl) | $-(-O(-C)_n-(C)_m-Y-)-$ | Z | B.P. (°C./pressure) or M.P. °C. |
|---|---|---|---|---|---|---|
| 91a | 2-methylpyridine | O | p-phenylene | $-O-CH_2-CH-O-CH_3$ | 2-methylthiophene | 230° C./0.1 mm |
| 91b | 2-methylpyridine | $-CH_2O-$ | p-phenylene | $-O-CH_2-CH-O-CH_3$ | 2-pyridyl | 240° C./0.1 mm |
| 91c | 6-methyl-2-chloropyridine | O | p-phenylene | $-O-CH_2-CH-O-CH_3$ | 2-methylthiophene | 230° C./0.1 mm |
| 91d | 2-methylpyridine | S | p-phenylene | $-O-CH_2-CH-O-CH_3$ | 2-pyridyl | 240° C./0.2 mm |
| 91e | 2-methylpyridine | O | p-phenylene | $-O-CH_2-CH-CH_3$ | 3-chloro-2-methylpyridine | 240° C./0.1 mm |
| 91f | 2-methylpyridine | O | p-phenylene | $-O-CH_2-O-CH_2-CH_3$ | 2-pyridyl | 240° C./0.1 mm |
| 91g | 4-chloro-6-methyl-2-methoxypyridine | O | p-phenylene | $-O-CH_2-CH-O-CH_3$ | 2-pyridyl | 250° C./0.1 mm |

Preparation Examples for Process 2c

| Ex. No. | Het | X | R¹ | $[-O-(C)_n-(C-C)_p-Y-]$ | Z | B.P. (°C./pressure) or M.P. °C. |
|---|---|---|---|---|---|---|
| 92 | 2-pyridyl | O | 1,4-phenylene | —O—CH₂CH₂—O— | 6-methyl-2-pyridyl | 220–240° C./ 0.3 mm |
| 93 | 3-chloro-2-pyridyl | O | 1,4-phenylene | —OCH₂CH—CH₂—O—<br>                CH₃ | 2-chloro-3-pyridyl | 230–240° C./ 0.2 mm |
| 94 | 5-(methoxycarbonyl)-2-pyridyl (H₃CO—C(=O)—) | O | 1,4-phenylene | —OCH₂CH₂—O— | phenyl | 225–240° C./ 0.3 mm |
| 95 | 2-pyridyl | —CH₂—O— | 1,4-phenylene | —O—CH₂CH₂—O— | phenyl | 220° C./0.4 mm |
| 96 | 2-pyridyl | —O— | 1,4-phenylene | —O—CH₂—CH₂—S— | phenyl | 225–230° C./ 0.4 mm |

General procedure

A mixture of 1 mol of the compound of the formula (VI) and the approximately 0.8- to 1.5-fold molar amounts of compound of the formula (VII), the approximately 2- to 3-fold molar amount of K₂CO₃ powder and the approximately 0.02-fold amount of the phase transfer catalyst TDA-1 are stirred at 80° to 160° C. in dry acetonitrile for about 8 to 36 hours. After cooling, the acetonitrile is removed in vacuo, H₂O is added to the residue remaining and the mixture is extracted using an organic solvent. The combined organic phases are concentrated in vacuo after drying over Na₂SO₄ (for example). The resultant product is purified further by bulb tube distillation, recrystallization or column chromatography.

The following compounds are obtained according to this procedure.

Preparation Examples for Process 2d

General Procedure

A mixture of 1 mol of the compound of the formula (VIII) and the approximately 3- to 6-fold molar amount of compound of the formula (IX), the approximately 2- to 3-fold molar amount of K₂CO₃ powder, the approximately 4-fold molar amount of NaOH powder and the approximately 0.02-fold molar amount of the phase transfer catalyst TDA-1 are heated to reflux in toluene for about 36 hours. After cooling, the toluene phase is washed with water, dried over Na₂SO₄ and concentrated in vacuo. The resultant product is purified further by bulb tube distillation, recrystallization or column chromatography.

The following compounds are obtained according to this procedure.

| Ex. No. | Het | X | R¹ | $[-O-(C)_n-(C-C)_p-Y-]$ | Z | B.P. (°C./pressure) or M.P. °C. |
|---|---|---|---|---|---|---|
| 97 | pyrazin-2-yl | O | 1,3-phenylene (methyl-substituted) | —O—CH₂CH₂—O— | pyrazin-2-yl | yellow wax |

-continued

| Ex. No. | Het | X | R¹ | [O(C)ₙ(C-C)ₒ]ₚY | Z | B.P. (°C./pressure) or M.P. °C. |
|---|---|---|---|---|---|---|
| 98 | 5-CF₃, 2-pyridyl | O | 1,3-phenylene | —OCH₂CH₂O— | 5-CF₃, 2-pyridyl | 230–240° C./0.2 mm |
| 99 | 3-Cl, 2-pyridyl | O | 1,4-phenylene | —O—CH₂CH₂O— | 3-Cl, 2-pyridyl | 210–230° C./0.3 mm 180° C. |
| 100 | 5-Cl, 2-pyridyl | O | 1,4-phenylene | —S—CH₂CH₂O— | 5-Cl, 2-pyridyl | 215–230° C./0.3 mm |
| 101 | 5-Cl, 2-pyridyl | O | 1,4-phenylene | —OCH₂CH₂O— | 5-Cl, 2-pyridyl | 220–230° C./0.3 mm |
| 102 | 3-CF₃, 2-pyridyl | O | 1,3-phenylene | —OCH₂CH₂O— | 3-CF₃, 2-pyridyl | 230–240° C./0.2 mm |
| 103 | 6-Cl, 2-pyridyl | O | 1,4-phenylene | —OCH₂CH₂—O— | 6-Cl, 2-pyridyl | 230° C./0.2 mm |
| 104 | 2-pyridyl | O | 1,3-phenylene | —OCH₂CH₂—O— | 2-pyridyl | 220–230° C./0.4 mm |
| 105 | 5-CF₃, 3-Cl, 2-pyridyl | O | 1,3-phenylene | —OCH₂CH₂—O— | 5-CF₃, 3-Cl, 2-pyridyl | 240–250° C./0.1 mm |
| 106 | 2-pyridyl | CH₂O | 1,3-phenylene | —OCH₂CH₂O—CH₂— | 2-pyridyl | 230° C./0.3 mm |
| 107 | 5-Br, 2-pyridyl | O | 1,4-phenylene | —OCH₂CH₂—O— | 5-Br, 2-pyridyl | 230° C./0.2 mm |
| 108 | 2-benzothiazolyl | O | 1,4-phenylene | —O—CH₂CH₂—O— | 2-benzothiazolyl | 250° C./0.1 mm |

What is claimed is:
1. A substituted heteroaryl phenyl ether of the formula

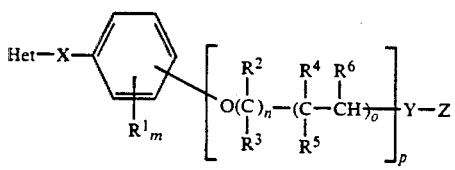

in which
Het represents pyridyl or pyridyl substituted by halogen, $C_1$-$C_4$-alkyl, 1-5-halogeno-$C_{1-2}$-alkyl, $C_{1-4}$-alkoxy, $C_{1-4}$-alkylmercapto, 1-3-halogeno-$C_{1-2}$-alkoxy, or 1-3-halogeno-$C_{1-2}$-alkylmercapto;

X represents O, S, —$CH_2$—, —O—$CH_2$—, —S—$CH_2$—, —$CH_2$—O—,

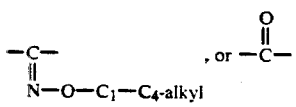

Y represents O, —O—$CH_2$— or S;

Z represents phenyl, pyridyl, or phenyl or pyridyl substituted by halogen, $C_1$-$C_4$-alkyl, 1-5-halogeno-$C_{1-2}$-alkyl, $C_{1-4}$-alkoxy, $C_{1-4}$-alkylmercapto, 1-3-halogeno-$C_{1-2}$-alkoxy, or 1-3-halogeno-$C_{1-2}$-alkylmercapto;

m represents integers from 1–4;
n represents 0, 1, 2, 3, or 4;
o represents 0, 1, 2, 3, or 4 provided that n and o do not simultaneously represent 0;
p represents integers from 1–4;
$R^2$, $R^3$, $R^4$, $R^5$ and $R^6$ independently of one another represent hydrogen or $C_1$-$C_6$-alkyl which is unsubstituted or substituted by halogen or $C_{1-4}$-alkoxy, or two radicals adjacent to one another can also, together with the C atoms to which they are bonded, form a saturated carbocyclic 5- or 6-membered ring;
$R^1$ represents identical or different substituents selected from the group consisting of hydrogen, halogen, CN, $C_{1-4}$-alkyl, 1-5-halogeno-$C_{1-4}$-alkyl, $C_{1-4}$-alkoxy, $C_{1-4}$-alkylthio, 1-5-halogeno-$C_{1-4}$-alkoxy, 1-5-halogeno-$C_{1-4}$-alkylthio, phenyl or phenoxy;

said phenyl ethers can be present in the form of their enantiomers, racemates or diastereomers.

2. A substituted heteroaryl phenyl ether according to claim 1, in which
X represents 0;
$R^1$ represents identical or different hydrogen, halogen, CN, $C_{1-4}$-alkyl, $C_{1-4}$-alkoxy, 1-3-halogeno-$C_{1-2}$-alkoxy, or phenyl radicals;
$R^2$, $R^3$, $R^4$, $R^5$ and $R^6$ independently of one another represent hydrogen, $C_{1-4}$-alkyl, 1-3halogeno-$C_{1-2}$-alkyl or $C_{1-2}$-alkoxy-$C_{1-4}$-alkyl,
m represents integers from 1–4
n represents 0, 1, 2, 3, 4
O represents 0, 1. 2, 3, 4,
provided that n and o do not simultaneously represent 0
p represents integers from 1–4.

3. A substituted heteroaryl phenyl ether according to claim 1, in which

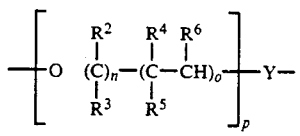

represents one of the following structures:

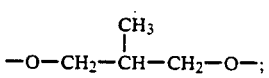

—O—$CH_2$—C($CH_3$)$_2$—$CH_2$—O—;

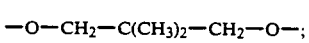

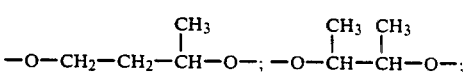

—O—$CH_2$—CH=CH—$CH_2$—O—;

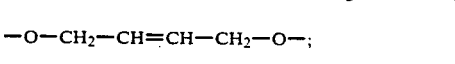

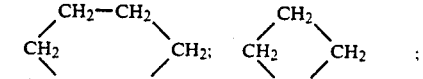

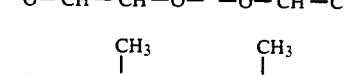

4. A substituted heteroaryl phenyl ether according to claim 1, in which
Het represents pyridyl heteroaromatic radical which is bonded to the phenyl ether via a C atom of the heteroaromatic and which is unsubstituted or substituted by chlorine, bromine, methyl, ethyl, trifluoromethyl or methoxy;
X represents 0;
$R^1$ represents hydrogen;

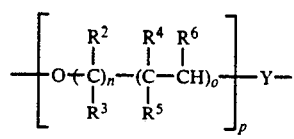

is in the para- or meta-position to the radical Het-X- and represents one of the following structures:

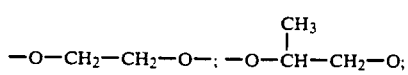

Z represents unsubstituted or substituted pyridyl heteroaromatic radical, which is bonded to the phenyl ether via a C atom of the heteroaromatic radical and phenyl or unsubstituted or substituted phenyl said substituents being fluorine, chlorine, bromine, methyl or trifluoromethyl.

5. A method of combating insects comprising applying to said insects, host animals of said insects or an insect environment an effective amount of at least one substituted heteroaryl phenyl according to claim 1.

6. A method according to claim 5, wherein said insects are fleas.

7. An insecticidal composition comprising at least one substituted heteroaryl phenyl ether according to claim 1 and a suitable carrier, excipient or extender therefor.

8. An insecticidal composition according to claim 7 wherein the insects are fleas.

* * * * *